(12) United States Patent
Tazi et al.

(10) Patent No.: US 9,556,489 B2
(45) Date of Patent: Jan. 31, 2017

(54) USE OF RBM39 AS A BIOMAKER

(71) Applicants: ABIVAX, Paris (FR); CENTRE NATIONAL DE LA RECHERCHE SCIENTIFIQUE (CNRS), Paris (FR); UNIVERSITE DE MONTPELLIER, Montpellier (FR); INSTITUT CURIE, Montpellier (FR)

(72) Inventors: Jamal Tazi, Clapiers (FR); Julian Venables, Newcastle (GB); Aude Garcel, Le Cres (FR); Noëlle Campos, Le Crés (FR); Florence Mahuteau-Betzer, Saint-Remy-les-Chevreuse (FR); Romain Najman, L'Hay-les-Roses (FR); Didier Scherrer, Castelnau le Lez (FR)

(73) Assignees: ABIVAX, Paris (FR); CENTRE NATIONAL DE LA RECHERCHE SCIENTIFIQUE (C.N.R.S.), Paris (FR); UNIVERSITE DE MONTPELLIER, Montpellier (FR); INSTITUT CURIE, Montpellier (FR)

( * ) Notice: Subject to any disclaimer, the term of this patent is extended or adjusted under 35 U.S.C. 154(b) by 0 days.

(21) Appl. No.: 14/383,395

(22) PCT Filed: Mar. 4, 2013

(86) PCT No.: PCT/IB2013/051707
§ 371 (c)(1),
(2) Date: Sep. 5, 2014

(87) PCT Pub. No.: WO2013/132412
PCT Pub. Date: Sep. 12, 2013

(65) Prior Publication Data
US 2015/0072892 A1 Mar. 12, 2015

(30) Foreign Application Priority Data
Mar. 5, 2012 (FR) .................................. 12 51980

(51) Int. Cl.
C12Q 1/68 (2006.01)
G01N 33/50 (2006.01)
C12Q 1/70 (2006.01)

(52) U.S. Cl.
CPC ......... *C12Q 1/6883* (2013.01); *G01N 33/5023* (2013.01); *C12Q 1/703* (2013.01); *C12Q 2600/106* (2013.01); *C12Q 2600/136* (2013.01); *C12Q 2600/158* (2013.01); *G01N 2500/10* (2013.01)

(58) Field of Classification Search
None
See application file for complete search history.

(56) References Cited

U.S. PATENT DOCUMENTS

2004/0086500 A1 5/2004 Bahr et al.

FOREIGN PATENT DOCUMENTS

WO WO 2010/039778 A2 4/2010
WO WO 2010/143169 A2 12/2010

OTHER PUBLICATIONS

French Search Report issued in FR 1251980 issued Oct. 19, 2012 (with translation).
French Written Opinion issued in FR 1251980 issued Oct. 19, 2012 (with translation).
International Search Report issued in PCT/IB2013/051707 mailed Jun. 19, 2013 (with translation).
Written Opinion of the International Searching Authority issued in PCT/IB2013/051707 mailed Jun. 19, 2013.
Venables et al., "Cancer-associated Regulation of Alternative Splicing," *Nature Structural & Molecular Biology*, Jun. 2009, vol. 16, No. 6, pp. 670-677.
Venables et al., "Cancer-associated Regulation of Alternative Splicing: Online Supplementary Table," *Nature Structural & Molecular Biology*, May 17, 2009, http://www.nature.com/nsmb/journal/v16/n6/suppinfo/nsmb.1608_S1.html.
Gautier et al., "In Vitro Nuclear Interactome of the HIV-1 Tat Protein," *Retrovirology*, May 19, 2009, vol. 6, pp. 1-18.
Gautier et al., "In Vitro Nuclear Interactome of the HIV-1 Tat Protein: Online Supplementary Table," *Retrovirology*, May 19, 2009, http://www.biomedcentral.com/content/supplementary/1742-4690-6-47-S1.xls.
Morou et al., "The HIV-1 gp120/V3 Modifies the Response of Uninfected CD4 T cells to Antigen Presentation: Mapping of the Specific Transcriptional Signature," *Journal of Translational Medicine*, 2011, vol. 9, pp. 1-16.
Dailly et al., "Virological Response to Darunavir in Patients Infected with HIV is Linked to Darunavir Resistance-associated Mutations Corrected by the Count of Mutations with Positive Impact and is not Associated with Pharmacological and Combined Virological/Pharmacological Parameters," *Fundamental and Clinical Pharmacology*, 2011, vol. 26, pp. 538-542.
König et al., "Impact of Drug Transporters on Cellular Resistance Towards Saquinavir and Darunavir," *Journal of Antimicrobial Chemotherapy*, 2010, vol. 65, pp. 2319-2328.

*Primary Examiner* — Jim Ketter
(74) *Attorney, Agent, or Firm* — Oliff PLC

(57) ABSTRACT

The present invention relates to the use (i) of a level of expression of a long RBM39 protein isoform, termed RBM39L, and (ii) of a level of expression of a short RBM39 protein isoform, termed RBM39C, as a marker for the efficacy of an active agent capable of preventing and/or treating HIV infection.

16 Claims, 2 Drawing Sheets

SEQUENCE LISTING

<160> NUMBER OF SEQ ID NOS: 3

<210> SEQ ID NO 1
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: Synthetic Construct

<400> SEQUENCE: 1
gcaatctctt cccgaacacg                                               20

<210> SEQ ID NO 2
<211> LENGTH: 18
<212> TYPE: DNA
<213> ORGANISM: Artificial Sequence
<220> FEATURE:
<221> NAME/KEY: source
<222> LOCATION: 1..18
<223> OTHER INFORMATION: Synthetic Construct

<400> SEQUENCE: 2
tcatggccgt tggcactg                                                 18

<210> SEQ ID NO 3
<211> LENGTH: 40
<212> TYPE: PRT
<213> ORGANISM: Homo sapiens
<220> FEATURE:
<221> NAME/KEY: SOURCE
<222> LOCATION: 1..40
<223> OTHER INFORMATION: Synthetic Construct

<400> SEQUENCE: 3

Met Ala Asp Asp Ile Asp Ile Glu Ala Met Leu Glu Ala Pro Tyr Lys
1               5                   10                  15

Lys Thr Cys Leu Thr Ile Ser His Leu Tyr Ser His Glu Phe Thr Phe
            20                  25                  30

Asp Ser Ser Val Asn Cys Gln Ser
        35                  40

USE OF RBM39 AS A BIOMAKER

Figure 1A:
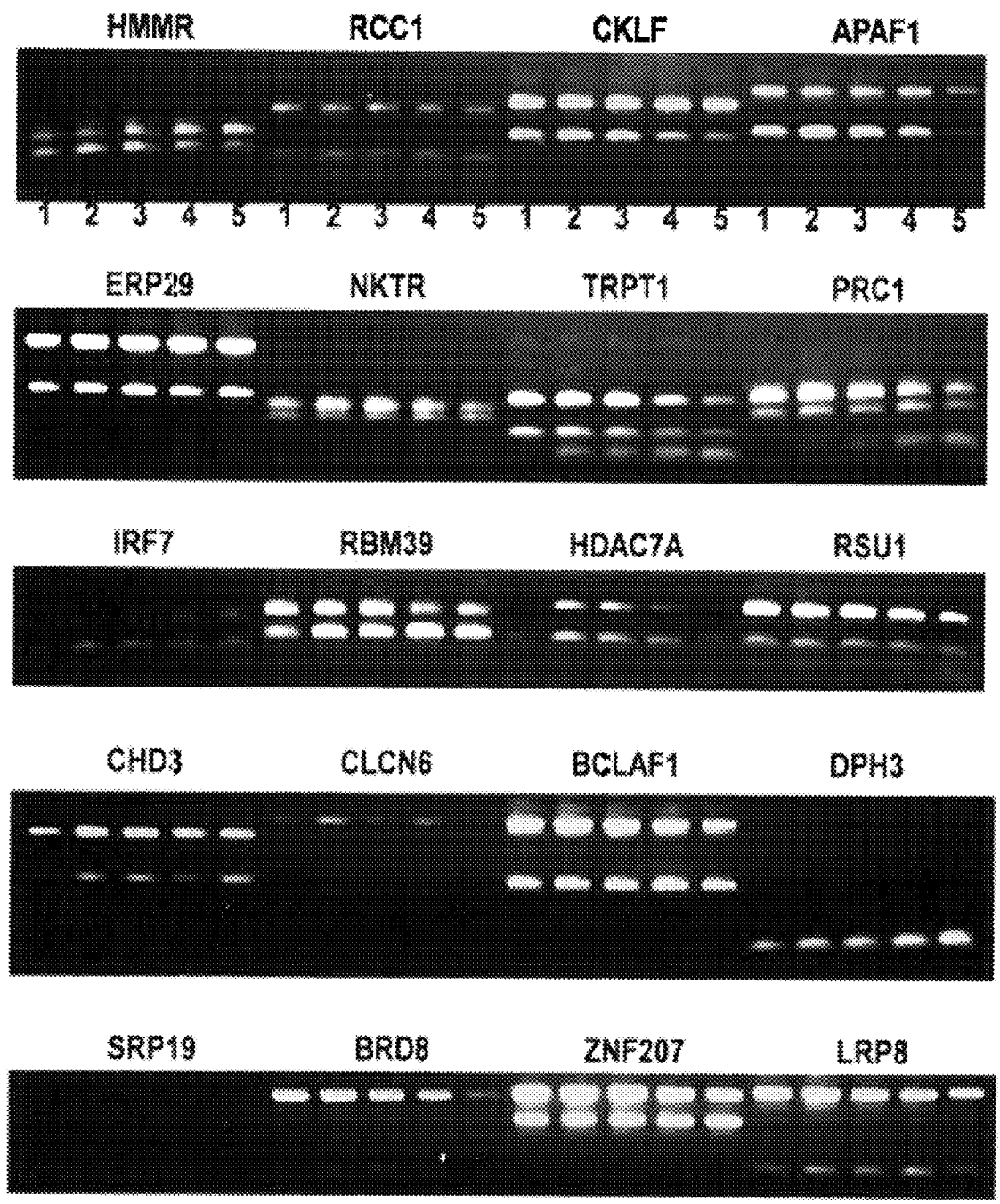

The present invention relates to a cellular marker for the human immunodeficiency virus (HIV). More specifically, the present invention relates to the identification of a cellular marker useful for evaluating the efficacy of compounds presumed to be active with respect to HIV. More particularly, the present invention relates to methods for screening new compounds that are active with respect to HIV or for evaluating the efficacy of a treatment with respect to HIV in a patient.

AIDS (acquired immunodeficiency syndrome) is an important global cause of mortality, and is considered to be pandemic. The infectious agent causing AIDS is the human immunodeficiency virus (HIV), a retrovirus belonging to the lentivirus family. This virus affects the T lymphocytes, leading to severe immunodeficiency and to the development of various cancers and opportunistic infections, and generally to the death of the infected individual.

Intracellular splicing is a process consisting of removing the introns from the messenger RNA (mRNA) to produce a mature mRNA, usable by the cell's translation machinery (Sharp, *Cell,* 1994, 77: 805). In the case of alternative splicing, the same precursor mRNA may be, through excision of certain exons, the source of various mRNAs coding for different forms of a protein, or isoforms, having distinct functions (Black, *Ann Rev Biochem,* 2003, 72: 991). These events are called alternative splicing events (ASE). The precise selection of the splicing sites at 5' and 3' is a mechanism that is a source of diversity, and which may lead to regulation of expression of the genes according to the tissue type or during development of the organism.

Sequencing of the human genome and analysis of EST (Expressed Sequence Tag) databases have shown that 65% of genes are expressed in the form of alternatively spliced variants (Ewin and Green, *Nat Genet,* 2000, 25: 232; Johnson et al., *Science,* 2003, 302: 2141). Moreover, it is estimated that 50% of the point mutations implicated in genetic diseases induce aberrant alternative splicing.

This mechanism may therefore constitute an interesting therapeutic target, and not only in the context of genetic diseases.

Thus, recently, new compounds acting on the alternative splicing process have been proposed for treating and/or preventing HIV infection (WO 2010/143169).

As the cellular mechanism of alternative splicing is a particularly interesting therapeutic target for treating HIV infection, there is a need for a cellular biomarker for evaluating the efficacy of potential active substances with respect to this mechanism.

There is also a need for a cellular biomarker useful for screening new active substances able to prevent and/or treat an HIV infection, and acting on alternative splicing.

There is also a need for a biomarker allowing evaluation of the response of an individual with an HIV infection to treatment of this infection.

The present invention aims to meet these needs.

Thus, according to one of these first aims, the present invention relates to the use of (i) an expression level of a long isoform of an RBM39 protein, called RBM39L, and (ii) an expression level of a short isoform of an RBM39 protein, called RBM39S, as a marker of the efficacy of an active substance suitable for preventing and/or treating an HIV infection.

In the sense of the invention, "isoform" means a particular form of a protein obtained by alternative splicing. Protein isoforms obtained from alternative splicing of an mRNA resulting from the transcription of one and the same gene have similar peptide sequences, but differ from one another by the addition or loss of a portion of their peptide sequence, resulting from the inclusion or the exclusion of an exon.

In the sense of the invention, "transcript" means a ribonucleic acid (RNA) resulting from the transcription of a gene. A gene can give several transcripts or mRNAs by alternative splicing, each coding for an isoform, obtained after translation of the mRNA.

In the sense of the invention, "expression" of an isoform of a protein means (i) either the synthesis of an mRNA encoding said protein isoform, by transcription of the corresponding gene, (ii) or the synthesis of said protein isoform by translation, and if necessary post-translational modification, of the mRNA encoding said protein isoform.

In the sense of the invention, cellular "marker" or "biomarker" means a constituent of a cell or of a tissue that may be determined directly or indirectly, for example by direct visualization or after sampling and labeling, for example with a fluorescent or isotopic marker, or else by an assay technique, and which is indicative of a physiological, biochemical or morphological state of said cell or of said tissue. Thus, a cellular marker or a biomarker may be used for qualifying a physiological, biochemical or morphological state of an individual requiring this or of a biological tissue of said individual.

In the sense of the invention, "prevent" refers to the action of reducing the risk of occurrence of an event.

The inventors observed, unexpectedly, a shift of the alternative splicing event (ASE) of the mRNA resulting from the transcription of the RBM39 gene toward the mRNA coding for the long isoform, mRNA-L, relative to an mRNA coding for the short isoform, mRNA-S, of the RBM39 protein, during the treatment of peripheral blood mononuclear cells with compounds that are active with respect to an HIV infection. It has been found that the ratio of the transcription level of mRNA-L to the sum of the transcription levels of mRNA-L and mRNA-S obtained from the RBM39 gene may be employed as a sensitive and specific marker of the efficacy of agents that are active with respect to an HIV infection.

The active agents considered in the invention are agents that are presumed to be active with respect to HIV and are presumed to be able to affect the alternative splicing of genes, and notably the ratio of the different mRNAs transcribed, and in consequence the ratio of the different protein isoforms produced.

According to another aspect, the present invention relates to a method for screening an active substance that is presumed to prevent and/or treat an HIV infection comprising at least the steps consisting of:
  a—bringing in contact:
   i—at least one cell suitable for the transcription, by alternative splicing, of an mRNA coding for a long isoform, mRNA-L, and of an mRNA coding for a short isoform, mRNA-S, of an RBM39 protein, said cell being disposed in conditions that are favorable to said transcription, and
   ii—an active substance to be screened,
  in conditions favorable to observation of any effect of said active substance on the transcription of an RBM39 gene,
  b—determining a transcription level of said short isoform and a transcription level of said long isoform of said RBM39 gene,
  c—determining a ratio of the transcription levels determined in step b), d—comparing said ratio obtained in step c) with a reference ratio.

The uses and methods of the invention are suitable for application in vitro, ex vivo or in vivo, and in particular in vitro or ex vivo.

According to yet another of these aims, the present invention relates to a method of evaluating the efficacy of an active substance intended for preventing and/or treating an HIV infection in an individual in need thereof comprising at least the steps consisting of:
- a—determining, in a biological sample isolated from said individual, before treatment with said active substance, an expression level of a long isoform of an RBM39 protein, RBM39L, and an expression level of a short isoform of an RBM39 protein, RBM39S,
- b—determining a ratio of the expression levels determined in step a),
- c—determining, in a biological sample isolated from said individual, after treatment with said active substance, an expression level of a long isoform of an RBM39 protein, RBM39L, and an expression level of a short isoform of an RBM39 protein, RBM39S,
- d—determining a ratio of the expression levels determined in step c), and
- e—comparing said ratio obtained in step d) with said ratio obtained in step b).

According to certain embodiments of the above method, said expression levels consist respectively of (i) a transcription level of an mRNA coding for a long isoform, mRNA-L, and (ii) a transcription level of an mRNA coding for a short isoform, mRNA-S, of an RBM39 protein.

According to certain other embodiments of the above method, said expression levels consist respectively of (i) a level of production of a long isoform, ProtL, and of (ii) a level of production of a short isoform, ProtS, of an RBM39 protein.

In the sense of the invention "isolated biological sample" refers to any biological sample obtained, and isolated, from an individual, and that is presumed to be suitable for determining a transcription level of the long and short isoforms of the RBM39 protein. For example, an isolated biological sample suitable for the invention may be a blood sample and may comprise mononuclear cells.

According to yet another of these aims, the present invention relates to a use of a kit comprising at least one pair of nucleic acid primers suitable for determining a transcription level of an mRNA coding for a long isoform, mRNA-L, and a transcription level of an mRNA coding for a short isoform, mRNA-S, of a protein.

The present invention has the advantage of offering a new sensitive, specific, and reproducible cellular marker for qualifying the efficacy of active agents with respect to HIV and acting on alternative splicing.

The present invention also has the advantage of offering sensitive, rapid and simple methods for determining the efficacy of active agents with respect to an HIV infection.

RBM39 Protein

The RBM39 protein (or RNA-binding protein 39) is present in the nucleus, where it is co-localized with proteins of the spliceosomal nucleus. It is an RNA-binding protein that functions both as a splicing factor and as a factor regulating gene transcription (Dowhan et al., *Mol Cell*, 2005, 17: 429). Studies of the paralogous protein in the mouse suggest that this protein may act as a co-activator of transcription for JUN/AP-1 and the estrogen receptors (Jung et al., *J Biol Chem*, 2002, 277: 1229). RBM39 is also implicated as an oncogenic co-factor (Dutta et al., *J Virol*, 2008, 82: 10792) and is implicated in alternative splicing of the angiogenesis factor VEGF (Dowhan et al., 2005). Finally, RBM39 has recently been identified as a factor interacting with the tat protein of HIV by a proteomic strategy based on affinity chromatography coupled to a mass spectrometer (Gautier et al., *Retrovirology*, 2009, 6: 47).

It is to be noted that the RBM39 gene consists of the nucleic acid from the nucleotide in position 34330259 to the nucleotide in position 34291128 of the "minus" strand of human chromosome 20 as referenced in the GenBank database.

A plurality of isoforms of the RBM39 protein is known. The plurality of isoforms of the RBM39 protein results from the existence of a great variety of transcription products of the RBM39 gene, owing to alternative splicing events. About 57 distinct mRNAs and about 34 isoforms of the RBM39 protein are currently listed.

Exclusively (i) the long isoform and (ii) the short isoform, whose expression levels are used as a marker for the present invention, are documented below.

A first isoform, called "long isoform" for the purposes of the present description, or isoform 1 or HCC1.4 (UniProtKB/Swiss-Prot reference Q14498-1) comprises 530 amino acids and has a molecular weight of about 59 380 Da.

Said long isoform is encoded by an mRNA, called mRNA-L, whose nucleotide sequence is known (GenBank references "transcript_id: NM_184234.2", "db_xref: GI:336176061"; "db_xref: GeneID:9584"; "db_xref: HGNC:15923"; "db_xref:HPRD:09201"; "db_xref: MIM: 604739").

A second isoform, called "short isoform" for the purposes of the present description, comprises 40 amino acids and has a molecular weight of about 4500 Da. Said short isoform is represented by the amino acid sequence SEQ ID No. 3.

The short isoform results from alternative splicing causing insertion of an additional exon, between exon No. 2 and exon No. 3 present on the mRNA encoding the long isoform. The additional exon (exon "No. 3" present on the mRNA encoding the short isoform) causes (i) a change of the reading frame and (ii) insertion of a stop codon.

Said short isoform is encoded by an mRNA, called mRNA-S. More precisely, the short isoform of sequence SEQ ID No. 3 is encoded by a plurality of messenger RNAs, all of which result from an event of insertion of said additional exon causing a change of the reading frame and the introduction of said stop codon. The different messenger RNAs encoding the short isoform of RBM39 of sequence SEQ ID No. 3 are collectively designated "mRNA-S" in the present description.

The amino acid sequence from the residue in position 1 to the residue in position 17 of the sequence of the short isoform of SEQ ID No. 3 is identical to the amino acid sequence from the residue in position 1 to the residue in position 17 of the sequence of 530 amino acids of the long isoform (UniProtKB/Swiss-Prot reference Q14498-1). However, owing to the change of the reading frame generated by the presence of the additional exon in mRNA-S, the sequence from residue 18 to residue 40 of the short isoform of sequence SEQ ID No. 3 differs from the corresponding sequence of said long isoform.

It is shown according to the invention that when the RBM39 gene is transcribed physiologically in the cells of the immune system, the mRNAs (collectively mRNA-S) coding for the short isoform are transcribed predominantly relative to the mRNA coding for the long isoform.

It is to be noted that there is no relation specifically between (i) the length of an isoform of the RBM39 protein and (ii) the length of the mRNA encoding said isoform. To illustrate this point, the mRNA-L that encodes the long isoform of RBM39 is shorter than the mRNA-S that encodes the short isoform of RBM39. The increased length of mRNA-S, relative to mRNA-L, results from the presence of the additional exon generating an early stop codon in mRNA-S.

It is to be noted that the mRNA-L may easily be discriminated from the messenger RNAs encoding the short isoform (collectively mRNA-S) owing to the shorter length of mRNA-L, relative to the length of each of the messenger RNAs encoding the short isoform.

Thus, a shift of the equilibrium of transcription of the gene encoding RBM39 to a reduction of the transcription level of mRNA-L compared to the transcription level of mRNA-S may indicate a change of the mechanisms of alternative splicing affecting the transcription of this gene, and more globally of the physiology of the cell and of the infections that may affect it.

It is to be noted that a shift of the equilibrium of transcription of the gene encoding RBM39 to a reduction of the transcription level of mRNA-L compared to the transcription level of mRNA-S induces a parallel shift of the equilibrium from the synthesis or production of the RBM39 protein to a reduction of the level of production of the long isoform ProtL compared to the level of production of the short isoform ProtS.

Uses and Methods

The uses and methods of the invention may, in particular, be suitable for qualifying or for screening an agent that is presumed to be active with respect to an HIV infection, or may be suitable for determining the efficacy of a treatment of an individual with an HIV infection by means of these active substances.

One aspect of the invention comprises determination of the expression levels of the short (RBM39S) and long (RBM39L) isoforms of an RBM39 protein.

This aspect comprises determination of the transcription levels of the mRNAs coding for the short (mRNA-S) and long (mRNA-L) isoforms of an RBM39 protein.

This aspect of the invention also comprises determination of the level of production of the long isoform, called ProtL, and short isoform, called ProtS, of an RBM39 protein.

The transcription level of mRNA-S and mRNA-L may be determined by measuring the amount of corresponding mRNA directly produced by the cell, or may be determined on DNA obtained by reverse transcription of the mRNA using a method allowing conservation of the proportion of the different mRNAs.

The level of production of ProtS and ProtL may be determined by measuring the amount of corresponding protein produced by the cell, for example by methods employing (i) either detectable means specifically recognizing simultaneously the two isoforms ProtS and ProtL of an RBM39 protein, (ii) or detectable means specifically recognizing just one of the two isoforms ProtS and ProtL of an RBM39 protein, which may be used in combination.

According to one aspect of the invention, determination of the transcription levels of the mRNAs may be performed on the whole mRNA or on a characteristic portion of the mRNA. A characteristic portion is a portion including some or all of the exon or exons forming the object of the alternative splicing.

Advantageously, determination of the transcription levels may be carried out on a characteristic portion of the mRNA-S and mRNA-L resulting from transcription of the RBM39 gene by a method comprising a step of specific amplification of this portion.

The methods for detecting and for measuring the amount of RNA or DNA are known by a person skilled in the art. These methods include the methods of RT-PCT (for "Reverse Transcriptase PCR") and qRT-PCR (for "quantitative Reverse Transcriptase PCR") and Real-Time PCR. For the application of these methods, a person skilled in the art may refer notably to the works of Wang et al. (1989, Proc Natl Acad Sci USA, Vol. 86: 917-921), of Wong et al. (2005, Bio Techniques, Vol. 39 (1): 75-85), of Nolan et al. (2006, Nat Protoc, Vol. 1(3): 1559-1582) and of Klinck et al. (2008, Cancer Research, Vol. 68: 657-663), or to a general review of these techniques published by Bustin (2000, Journal of Molecular Endocrinology, Vol. 25: 169-193).

All of these methods comprise (i) a step of extraction of the cellular mRNAs, (iii) a step of reverse transcription of the mRNA into DNA using a reverse transcriptase enzyme and (iii) a step of amplification of the DNA obtained in the preceding step, using suitable nucleotide primers, before quantification of the amplified DNA. In general, the following are amplified simultaneously starting from the same sample (a) the DNA obtained by reverse transcription of the mRNA of interest and (b) a DNA or a plurality of DNAs obtained by reverse transcription of mRNAs expressed constitutively and constantly by the cells ("housekeeping genes"), such as the RNAs encoded by the genes MRPL19, PUM1 and GADPH.

The amplified DNA may be quantified, after separation by electrophoresis, by measuring the bands of DNA, and the results for the mRNA or mRNAs of interest expressed in relative values by comparison with the mRNAs encoded by the "housekeeping" genes. In certain embodiments, the step of separation of the amplified DNAs is carried out by agarose gel electrophoresis, then staining of the bands of DNA with ethidium bromide, before quantification of the DNAs contained in the migration bands by densitometry. In other embodiments, a device with microchannels is used, in which the amplified DNAs are separated by capillary electrophoresis, and then the different DNAs separated are quantified by measuring the signal emitted by these DNAs after illumination with a laser beam. Such a device may be the LabChip® apparatus, for example of the "GX" series, marketed by the company Caliper LifeSciences (Hopkinton, Mass., United States).

In certain embodiments, determination of the transcription levels of the mRNAs may comprise a step of combined amplification of the cDNAs resulting from the reverse transcription of the mRNA-L and mRNA-S using a single pair of nucleotide primers, the two types of resultant amplified cDNA then being separated, preferably by electrophoresis.

In other embodiments, determination of the transcription levels of the mRNAs may comprise a step of amplification of a characteristic portion of the mRNA-L and mRNA-S resulting from transcription of the RBM39 gene, using two separate primer pairs, respectively for the cDNA obtained from each of mRNA-L and mRNA-S.

Various sense and antisense primers may be employed in a reaction of RT-PCR suitable for the invention, provided that they flank the exon forming the object of inclusion or exclusion. The choice of the sense and antisense primers may also be guided by the length differences between the transcripts obtained from the mRNA-L and mRNA-S to be amplified. The difference in length may be adjusted depending on the method of separation of the amplified transcripts and the degree of resolution that it provides.

Advantageously, primers suitable for the invention may be selected for amplifying a portion of mRNA of RBM39 that may include the additional exon, and comprising at least 18 nucleotides on either side of this exon.

Advantageously, the difference in size between the transcripts obtained from the mRNA-L and mRNA-S resulting from transcription of the RBM39 gene is 73 nucleotides.

In advantageous embodiments, a primer pair is selected in such a way that:
- a first primer hybridizes specifically to the region of an mRNA resulting from transcription of the RBM39 gene corresponding to exon No. 1 (exon referenced No. 1 in the mRNA-L encoding the long isoform). Exon No. 1 consists of the nucleic acid from the nucleotide in position 5001 to the nucleotide in position 5396 of the sequence of the RBM39 gene (GenBank reference No. NG_029955), and
- a second primer hybridizes specifically to the region of an mRNA resulting from transcription of the RBM39 gene corresponding to exon No. 3 (exon referenced No. 3 in the mRNA-L encoding the long isoform). Exon No. 3 consists of the nucleic acid from the nucleotide in position 6740 to the nucleotide in position 6812 of the sequence of the RBM39 gene (GenBank reference No. NG_029955).

Sense and antisense primers suitable for the invention may be obtained by any method known by a person skilled in the art in this field, notably as described by Sambrook et al. (Molecular Cloning: A Laboratory Manual, 3$^{rd}$ Ed., 2001, Cold Spring Harbor, N.Y.).

In certain embodiments, a pair of nucleotide primers is used comprising respectively the sequences SEQ ID No. 1 and SEQ ID No. 2. The nucleotide primer of sequence SEQ ID No. 1 hybridizes to a region of an mRNA resulting from transcription of the RBM39 gene, which comprises exon 3 of said gene (hybridizes to the complementary sequence of the nucleic acid comprising nucleotides 34329893 to 34329912 of the "minus" strand of chromosome 20 according to GenBank). The nucleotide primer of sequence SEQ ID No. 2 hybridizes to a region of an mRNA resulting from transcription of the RBM39 gene, which comprises exon 1 of said gene (hybridizes to the complementary sequence of the nucleic acid comprising nucleotides 34326905 to 34326922 of the "minus" strand of chromosome 20 according to GenBank).

According to one aspect of the invention, the transcription levels of mRNA-L and mRNA-S resulting from transcription of the RBM39 gene may be determined in the form of a ratio.

Advantageously, this ratio may be determined by establishing a ratio of a transcription level of the mRNA coding for a long isoform of an RBM39 protein to a transcription level of the mRNA coding for a short isoform of an RBM39 protein.

Even more advantageously, it is possible to establish a ratio of a transcription level of the mRNA coding for a long isoform of an RBM39 protein to the sum of the transcription levels of the mRNAs coding for the long and short isoforms of an RBM39 protein. This ratio makes it possible to determine a value as percentage splicing ($\Psi$).

According to another aspect of the invention, a ratio thus determined may be compared with a reference ratio.

In the sense of the invention, "reference ratio" refers to a ratio determined by means of transcription levels of mRNA measured in baseline conditions or qualified as physiologically normal.

For example, these transcription levels may be determined in cells disposed in physiological conditions or conditions imitating physiological conditions, and in the absence of external factors that may affect these conditions. An external factor considered in the invention may be an active agent that is presumed to be effective for preventing and/or treating an HIV infection.

A reference ratio may be obtained in parallel with the ratio determined in the presence of an external factor that may affect the transcription of the mRNAs of interest, or may be determined beforehand or even subsequently.

A reference ratio may be stored on a storage medium, for example electronic, to constitute a so-called reference database.

According to one aspect of the invention, when employing the invention for evaluating the efficacy of an active substance suitable for preventing and/or treating an HIV infection, a reference ratio may be obtained by determining the transcription level of the mRNAs of interest in the absence of the active substance whose efficacy is to be evaluated.

In particular, when employing the invention for screening an active substance that is presumed to prevent and/or treat an HIV infection, a reference ratio may be determined by reproducing the screening protocol in the absence of the active substance to be screened.

In particular, when employing the invention for evaluating the efficacy of an active substance intended for preventing and/or treating an HIV infection in an individual in need thereof, a reference ratio may be determined in an isolated biological sample obtained from said individual before administration of the active substance.

Alternatively, a reference ratio may be determined in a set of individuals who have not undergone the treatment whose efficacy is to be evaluated.

When employing the invention for evaluating the efficacy of an active substance intended for preventing and/or treating an HIV infection in an individual in need thereof, the reference ratio may, if applicable, be correlated with other parameters of the patient, such as his age, his weight or other pathophysiological parameters.

A deviation between a ratio determined in the presence of a factor that may affect the transcription level of the mRNAs of interest, such as an active agent, and a reference ratio may be indicative of a possible effect of said factor, such as said active agent.

Such a deviation may be indicative of a shift of the alternative splicing event from the transcription level of mRNA-L to the level of mRNA-S, of the mRNAs resulting from transcription of the RBM39 gene. Such a shift may be indicative of a possible effect of the factor investigated, such as the efficacy of an agent that is presumed to be active with respect to an HIV infection and acting on the alternative splicing mechanisms.

Such a deviation may result from a decrease in the value of the ratio of a transcription level of the mRNA coding for a long isoform of an RBM39 protein to the sum of the transcription levels of the mRNAs coding for the long and short isoforms of an RBM39 protein.

According to one aspect of the invention, a deviation between a ratio of the transcription levels of mRNA-L and mRNA-S coding for an RBM39 protein determined in the presence of an agent that is presumed to be active with respect to HIV and a reference ratio may be indicative of a possible effect of said active agent with respect to HIV.

According to another aspect of the invention, a deviation between a ratio of the transcription levels of mRNA-L and mRNA-S coding for an RBM39 protein determined in an individual treated with an agent that is presumed to be active with respect to HIV and a reference ratio may be indicative of a possible effect of said active agent with respect to HIV or of a sensitivity of the individual to the treatment.

Depending on the degree of deviation observed, an individual treated may be qualified as resistant, slightly resistant, slightly sensitive, or sensitive to the treatment.

Thus, application of the invention may also make it possible to determine the resistance, or the degree of resistance, or the sensitivity or the degree of sensitivity of the HIV infecting an individual to the treatment intended to be administered to said individual.

According to another aspect, the invention may be employed for monitoring the progression of the resistance of HIV to the anti-HIV treatment in an individual with an HIV infection.

Such an embodiment may comprise obtaining a first biological sample isolated from an individual with an HIV infection and who underwent an anti-HIV treatment at a time $t_0$, determining a ratio of the transcription levels of mRNA-L and mRNA-S coding for an RBM39 protein, and comparing the ratio obtained with a ratio of the transcription levels of mRNA-L and mRNA-S coding for an RBM39 protein determined in a second biological sample isolated from said individual at a later time $t_1$.

Observation of a deviation or of an absence of deviation between the two ratios determined may be indicative of the progression or absence of progression of the infection with HIV to the anti-HIV treatment. Obtaining additional biological samples isolated from said individual and determining the ratios of the transcription levels of mRNA-L and mRNA-S coding for an RBM39 protein may be carried out as many times as desired. The possibility of monitoring an individual by carrying out a series of determinations of ratios of transcription levels of mRNA-L and mRNA-S coding for an RBM39 protein over time may be used for monitoring the progression of the resistance of an HIV infection to the treatment administered.

According to another preferred embodiment, a method of the invention may employ a cell selected from the peripheral blood mononuclear cells, HeLa, Jurkat, CEM cells or any other cells that may be infected with the AIDS virus.

According to another preferred embodiment, in a method of the invention the transcription levels of the short and long isoforms of the RBM39 gene may be obtained using a method selected from RT-PCR, RTqPCR.

According to other embodiments of a method of the invention, the expression levels of the long isoform RBM39L and of the short isoform RBM39S of the RBM39 protein consist respectively of (i) a level of production of a long isoform, called ProtL, and (ii) a level of production of a short isoform, called ProtS, of an RBM39 protein.

In these embodiments, said expression levels are determined by methods comprising a step of quantifying the ProtL and ProtS produced by the cells.

Typically, the isoforms ProtL and ProtS may be detected and quantified using ligand compounds specifically recognizing (i) either the two isoforms ProtL and ProtS indifferently, (ii) or specifically just one of the two isoforms ProtS and ProtL, in which case two ligand compounds that are specific respectively to the isoform ProtL and the isoform ProtS are necessary.

The ligand compounds of the isoforms ProtS and ProtL may be selected from antibodies, nucleic aptamers and protein aptamers, the methods of production of which are well known by a person skilled in the art.

In particular, nucleic aptamers binding specifically to the isoform ProtL, or if applicable to the isoform ProtS, or else to both isoforms ProtL and ProtS, may be obtained by the SELEX technique described for example in the American patents U.S. Pat. No. 5,475,096 and U.S. Pat. No. 5,270,163.

Antibodies directed specifically against each of the isoforms ProtL and ProtS, and antibodies specifically recognizing both isoforms ProtS and ProtL simultaneously, may also be prepared by a great variety of techniques known by a person skilled in the art. Such antibodies include polyclonal antibodies and monoclonal antibodies, including the antibodies obtained by genetic recombination. The antibodies may be obtained following the teaching of Kohler and Milstein (1975, Nature, Vol. 256: 495-497). They may be obtained by genetic cloning techniques from a single lymphocyte from a suitably immunized animal, as described by Babcook et al. (1996, Proc Natl Acad Sci USA, Vol. 93(15): 7843-78841) or else in the PCT applications WO 9202551, WO 2004051268 and WO 2004106377. They may be recombinant antibodies, in particular humanized antibodies, and may be obtained by the techniques described in the American patent U.S. Pat. No. 5,585,089 or in the PCT application WO 91/09967, or else in the patent documents EP0546073, U.S. Pat. No. 5,545,806, U.S. Pat. No. 5,569,825, U.S. Pat. No. 5,625,126, U.S. Pat. No. 5,633,425, U.S. Pat. No. 5,661,016, U.S. Pat. No. 5,770,429, EP 0438474 and EP0463151.

Numerous antibodies specifically recognizing the RBM39 protein, and in particular specific regions of the RBM39 protein are commercially available. We may use for example any one of the anti-human RBM39 antibodies marketed by the company Sigma Aldrich, and notably the antibodies referenced respectively #SAB2101959, #SAB2103105 and #HPA001591. We may also use designated "Caper (P14) marketed by the company Santa Cruz Biotechnology Inc.

ELISA test kits for detecting or quantifying the RBM39 protein are also commercially available.

In certain embodiments of a method according to the invention, an antibody specifically recognizing the C-terminal region of the RBM39 protein (isoform ProtL) is used. As an antibody recognizing the C-terminal portion of RBM39, it is possible to use for example the antibody #A300-353A, which recognizes the epitope comprised in the region 480-530, marketed by the company Bethyl Laboratories (Montgomeryn Tex. USA). Alternatively, we may use the antibody #IHC-00022 also marketed by the company Bethyl Laboratories, which recognizes the region 325-375 of the RBM39 protein.

The isoforms ProtL and ProtS may be detected and quantified by techniques well known by a person skilled in the art, for example by an immunoblotting technique (also designated "Western Blotting"). Typically, the cellular proteins are submitted after extraction to a step of migration on electrophoresis gel; then the protein bands are incubated with the anti-RBM39 antibody, or else with a combination of antibodies recognizing ProtL and ProtS respectively. The isoforms ProtL and ProtS may be distinguished according to their position of migration on the electrophoresis gel. Then the isoforms ProtL and ProtS are quantified, for example by measuring a detectable signal emitted by the antibodies used, for example by fluorescence measurement if the anti-RBM39 antibodies, or else second anti-antibody antibodies if second antibodies are used, are labeled with a chromophore or a fluorophore, or else by absorbance measurement if said antibodies are coupled to an enzyme capable of catalyzing the formation of a product absorbing light at a given wavelength.

The present invention relates to a method for screening an active substance that is presumed to prevent and/or treat an HIV infection comprising at least the steps consisting of:
a—bringing in contact:
i—at least one cell suitable for production, by alternative splicing of mRNA, of a long isoform of the RBM39 protein, ProtL, and of a short isoform of the RBM39 protein, ProtS, said cell being disposed in conditions favorable to said production, and
ii—an active substance to be screened,
in conditions favorable to observation of any effect of said active substance on the transcription of an RBM39 gene,
b—determining a level of production of said short isoform and a level of production of said long isoform of said RBM39 protein,
c—determining a ratio of the levels of production determined in step b),
d—comparing said ratio obtained in step c) with a reference ratio.

In the sense of the invention, "reference ratio" refers, in the context of the above method, to a ratio determined from levels of production of proteins measured in baseline conditions or qualified as physiologically normal.

Advantageously, this ratio may be determined by establishing a ratio of a level of production of the long isoform of an RBM39 protein to a level of production of the short isoform of an RBM39 protein.

Even more advantageously, a ratio may be established between a level of production of the long isoform of an RBM39 protein and the sum of the levels of production of the long and short isoforms of an RBM39 protein. This ratio makes it possible to determine a value as percentage splicing ($\Psi$).

The details for carrying out the above methods with the values of levels of production of the isoforms ProtL and ProtS are easily determined by a person skilled in the art, from the teaching for carrying out the methods for which the expression levels of the isoforms of the RBM39 protein consist of transcription levels of an mRNA coding for said isoforms, which is disclosed in the present description.

The present invention also relates to a method of evaluating the efficacy of an active substance intended for preventing and/or treating an HIV infection in an individual in need thereof comprising at least the steps consisting of:
a—determining, in a biological sample isolated from said individual, before treatment with said active substance, a level of production of a long isoform of an RBM39 protein, ProtL, and an expression level of a short isoform of an RBM39 protein, ProtS,
b—determining a ratio of the levels of production determined in step a),
c—determining, in a biological sample isolated from said individual, after treatment with said active substance, a level of production of a long isoform of an RBM39 protein, ProtL, and a level of production of a short isoform of an RBM39 protein, ProtS,
d—determining a ratio of the levels of production determined in step c), and
e—comparing said ratio obtained in step d) with said ratio obtained in step b).

Kits

A kit suitable for a use of the invention may comprise at least one primer pair suitable for determining a transcription level of an mRNA coding for a long isoform, mRNA-L, and of a transcription level of an mRNA coding for a short isoform, mRNA-S, of an RBM39 protein.

The sense and antisense primers may be packaged in two separate containers or may be packaged in one and the same container. Besides these primers, a kit of the invention may comprise the set of enzymes and reagents necessary for carrying out the methods for detecting the transcripts of a gene, notably as detailed above.

A kit suitable for the invention may further comprise an explanatory notice specifying the ways of determining a ratio of the transcription levels of an mRNA coding for a long isoform, mRNA-L, and of an mRNA coding for a short isoform, mRNA-S, of an RBM39 protein and for comparing the ratio obtained with a reference ratio.

In other embodiments, a kit suitable for a use of the invention may comprise at least one antibody recognizing both the long isoform ProtL and the short isoform ProtS of the RBM39 protein, or alternatively at least two antibodies, respectively an antibody specifically recognizing the long isoform ProtL of the RBM39 protein and an antibody recognizing the short isoform ProtS of the RBM39 protein.

If applicable, the anti-RBM39 antibody or antibodies are labeled with a detectable molecule.

If applicable, said kit also comprises antibodies, called second antibodies, recognizing the anti-RBM39 antibodies, for example antibodies recognizing the Fc portion of the anti-RBM39 antibodies, said second antibodies being labeled with a detectable molecule, for example a chromophore molecule, a fluorophore molecule, or else an enzyme capable of catalyzing the transformation of a chromogenic substrate.

LEGEND OF THE FIGURES

FIG. 1: FIG. 1A illustrates the results obtained by RT-PCR and agarose gel electrophoresis with the 20 spots each nonspecifically associated with a compound and identified in example 1, in five conditions: (1) PBMC, (2) PBMC+ DMSO, (3) Darunavair, (4) drug402, and (5) drug464. The long and short isoforms are visible for the majority of the ASEs but a significant shift of splicing toward one or other of the isoforms could only be observed for the CKLF and RBM39 genes.

Figure 1B:
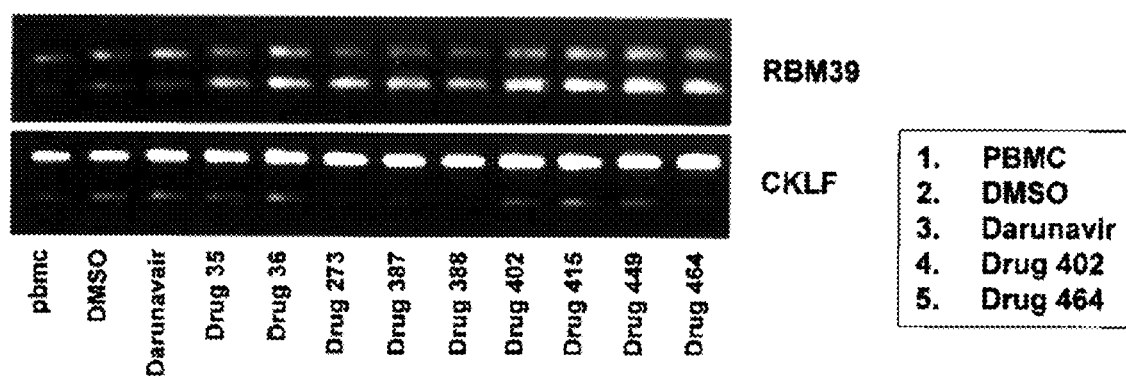

FIG. 1B illustrates a new determination of the ASEs for the CKLF and RBM39 genes in the same conditions as those used in example 1, and only the alternative splicing of the RBM39 gene was modified constantly by the test compounds. Transcription of the short isoform is induced by the test compounds to the detriment of expression of the long isoform.

The various aspects of the present invention are illustrated by the examples detailed below, which must not be interpreted as in any way limiting the scope of the invention.

EXAMPLES

Example 1

Identification of the Alternative Splicing Levels of RBM39 as a Marker of the Efficacy of an Active Substance Useful in the Treatment of an HIV Infection A. Materials and Methods
1. General Methodology The alternative splicing reactions investigated were selected following successive screenings of the RefSeq database and considering the alternative splicings known to be manifested sensitively and constantly in different cell lines.

To find a candidate marker, 382 alternative splicing events (Alternative Splice Event, ASE) were preselected and represent a random plate with high rate of global alterations of alternative splicing. Of the 382 ASEs preselected, only 309 ASEs could be detected satisfactorily in the PBMCs.

The 309 alternative splicing events (Alternative Splice Events or ASE) (y axis) were tested by PCR carried out on known regions of alternative splicings in twelve samples (x axis): PBMC (cells), PBMC+DMSO (DMSO), PBMC+control (Darunavair), PBMC+test compounds (drug387, drug464, drug273, drug388, drug449, drug36, drug35, drug402, drug415). Exclusion or inclusion of an exon leads to two different PCR products: a short isoform and a long isoform.

The compounds drug35 and drug36 correspond respectively to compounds C24 and C25 of WO 2009/087238 (WO 2009/087238, page 45). They are prepared as described in that document.

The compounds drug387, drug464, drug273, drug388, drug449 and drug402 are described in WO 2010/143169:
drug387 is compound 77, of formula Ib (page 51)
drug464 is compound 90, of formula Ib (page 53)
drug273 is compound 6, of formula Ia (page 44)
drug388 is compound 112, of formula Ie (page 56)
drug449 is compound 43, of formula Ia (page 47)
drug402 is compound 80, of formula Ib (page 52)
drug415 is compound 106, of formula Ic (page 56).

2. Technique Used

Peripheral blood mononuclear cells (PBMC) purified by centrifugation on a cushion of Ficoll® from bags of blood (healthy donors) supplied by the Paris Blood Transfusion Center (France).

The RNA is extracted from the cells by the Tri Reagent® method (Sigma) and the complementary DNAs of the mRNAs (cDNA) coding for the long and short isoforms of RBM39 are amplified by RT (Reverse transcriptase)-PCR in order to obtain the two splicing isoforms mRNA-L and mRNA-S. The commercial kit "First strand cDNA synthesis kit" marketed by the company GE HealthCare (United States) was used.

Typically, the RT-PCR reactions were carried out with 60 ng mRNA as substrate in a final reaction volume of 50 µl final containing 50 pmol of each primer, respectively (i) the sense primer: GCAATCTCTTCCCGAACACG (SEQ ID No. 1), and (ii) the antisense primer TCATGGCCGTTG-GCACTG (SEQ ID No. 2) and polymerase Taq Platinum® (Invitrogen company).

The conditions of the reactions of amplification of the cDNA by PCR are as follows: (a) 2 min at 94° C. then (b) 35 cycles of 30 s with the following sequences (b1) 94° C., (b2) 55° C. and (b3) 72° C., followed by (c) 2 min of elongation at 72° C.

The PCR products are analyzed on 1.5% agarose gel and the amplified fragments are visualized by staining with ethidium bromide.

For each alternative splicing event, twelve conditions were tested: PBMC (cells), PBMC+DMSO (DMSO), PBMC+control (Darunavair), PBMC+test compounds (the following compounds, respectively: drug387, drug464, drug273, drug388, drug449, drug36, drug35, drug402, drug415).

Each compound is tested after activation of the cells with 100 U/ml of IL2 and infection with HIV-1 as is described in the international application filed on 14 Jun. 2010 under No. PCT/IB2010/052651 in the names of Splicos, Centre National de la Recherche Scientifique, Institut Curie and University of Montpellier 2 and in the international application filed on 14 Jun. 2010 under No. PCT/IB2010/052652 in the names of Splicos, Centre National de la Recherche Scientifique, Institut Curie and University of Montpellier 2.

The first results related to the data generated by 3708 PCR reactions.

A splicing percentage by value (psi or $\Psi$) is calculated for each reaction by determining a ratio of the concentration of long isoform to the sum of the concentrations of the short and long isoforms or L/(L+S). The $\Psi$ values obtained are alternately color-coded in temperature maps. Red color indicates a shift of splicing toward exclusion of an exon and green color indicates a shift of splicing toward inclusion of an exon.

The $\Psi$ values were calculated both for the genes whose splicing was altered only by one or two of the test compounds and for the other genes whose splicing is altered by several or all of the test compounds.

Exclusion or inclusion of an exon leads to two different PCR products: a short isoform and a long isoform.

High-throughput PCR analysis of these alternative splicing events was carried out by the technique described by Klinck et al. (2008, *Cancer Res*, 2008, 68: 657).

B. Results

The ASEs were deemed significant if more than 75% of PCR product has migrated with the expected mobility (qualifying the purity of the reaction) and if the concentration of the total product expected in PCR was above 20 nM (degree of intensity of the reaction). 309 ASEs satisfying these selection conditions were identified in the 12 conditions tested, and are represented in the temperature map in FIG. 1A.

An ASE "spot" is defined for any shift of the ASE of more than 20% relative to a mean value determined on 3 control values. 40 ASE "spots" were thus defined: 20 ASE "spots" corresponding to a sporadic shift induced only by one or two compounds, called specific ASE "spots", and 20 ASE "spots" displaced in the same direction and induced by several or all of the test compounds, called nonspecific ASE "spots".

The 20 nonspecific ASE "spots" were tested once again by RT-PCR for the 5 conditions: PBMC, PBMC+DMSO, Darunavair, drug402 and drug464.

Analysis by agarose gel electrophoresis did not confirm a significant shift with respect to most of the ASE "spots" between the control sample and the treated sample, except for the "spots" relating to the RBM39 and CKLF genes (FIG. 1 A).

Two ASE "spots" relating to the RBM39 and CKLF genes were tested once again for the 12 initial conditions (FIG. 1B).

Only the shift of the ASE of the RBM39 gene was confirmed for all the test compounds.

These results show that determination of the transcription of the long and short isoforms of the RBM39 gene, and in particular a shift of the ASE of the RBM39 gene, may be employed as a biomarker of the efficacy of active agents with respect to HIV infection by action on the alternative splicing mechanism.

The invention claimed is:

1. A method for evaluating the efficacy of an active substance suitable for preventing and/or treating an HIV infection comprising:
   determining (i) an expression level of a long isoform of an RBM39 protein, called RBM39L, and
   determining (ii) an expression level of a short isoform of an RBM39 protein, called RBM39S;
   wherein a shift toward the expression level of the long isoform relative to the expression level of the short isoform is indicative of the efficacy of said active substance for preventing and/or treating the HIV infection.

2. The method as claimed in claim 1, wherein said expression levels consist respectively of (i) a transcription level of an mRNA coding for a long isoform, called mRNA-L, and (ii) a transcription level of an mRNA coding for a short isoform, called mRNA-S, of an RBM39 protein.

3. The method as claimed in claim 1, wherein said expression levels consist respectively of (i) a level of production of a long isoform, called ProtL, and (ii) a level of production of a short isoform, called ProtS, of an RBM39 protein.

4. The method as claimed in claim 1, wherein a ratio of the expression level of RBM39L to the sum of the expression levels of RBM39L and of RBM39S is determined.

5. The method as claimed in claim 1, wherein the expression levels consist of transcription levels and are determined by a technique of quantification with amplification of nucleic acids.

6. The method as claimed in claim 1, wherein the expression levels consist of levels of production and are determined by a method of immunodetection.

7. A method of screening in vitro or ex vivo of an active substance that is presumed to prevent and/or treat an HIV infection comprising at least the steps consisting of:
   a—bringing in contact:
      i—at least one cell suitable for the transcription, by alternative splicing, of an mRNA coding for a long isoform, mRNA-L, and of an mRNA coding for a short isoform, mRNA-S, of the RBM39 protein, said cell being disposed in conditions that are favorable to said transcription, and
      ii—an active substance to be screened, in conditions favorable to observation of a possible effect of said active substance on the transcription of an RBM39 gene, b—determining a transcription level of an mRNA-L and a transcription level of an mRNA-S of said RBM39 gene, c—determining a ratio of the transcription levels determined in step b), d—comparing said ratio obtained in step c) with a reference ratio;

wherein a shift toward the transcription level of the RBM39 gene toward the mRNA coding for the long isoform relative to the transcription level of the RBM39 gene toward the mRNA coding for the short isoform is indicative of the efficacy of said active substance for preventing and/or treating the HIV infection.

8. The method as claimed in claim 7, wherein the ratio determined in step c) consists of the ratio of the transcription level of mRNA-L to the sum of the transcription levels of mRNA-L and mRNA-S.

9. The method as claimed in claim 7, wherein a deviation between the ratio obtained in step c) and the reference ratio is indicative of a possible effect of said active substance to be tested.

10. The method as claimed in claim 7, wherein said cell is selected from the peripheral blood mononuclear cells, or any other cells that may be infected by HIV.

11. The method as claimed in claim 7, wherein the transcription levels of mRNA-L and mRNA-S coding for an RBM39 protein are obtained by means of a technique of quantification with amplification of nucleic acids.

12. A method as claimed in claim 1, comprising at least the steps consisting of:

a—determining, in a biological sample isolated from said individual, before treatment with said active substance, an expression level of a long isoform of an RBM39 protein, RBM39L, and an expression level of a short isoform of an RBM39 protein, RBM39S, b—determining a ratio of the expression levels determined in step a), c—determining, in a biological sample isolated from said individual, after treatment with said active substance, an expression level of a long isoform of an RBM39 protein, RBM39L, and an expression level of a short isoform of an RBM39 protein, RBM39S, d—determining a ratio of the expression levels determined in step c), and e—comparing said ratio obtained in step d) with said ratio obtained in step b).

13. The method as claimed in claim 12, wherein said expression levels consist respectively of (i) a transcription level of an mRNA coding for a long isoform, mRNA-L, and (ii) a transcription level of an mRNA coding for a short isoform, mRNA-S, of an RBM39 protein.

14. The method as claimed in claim 12, wherein said expression levels consist respectively of (i) a level of production of a long isoform, ProtL, and (ii) a level of production of a short isoform, ProtS, of an RBM39 protein.

15. The method as claimed in claim 1 comprising using a kit comprising at least one pair of nucleic acid primers suitable for determining a transcription level of an mRNA coding for a long isoform, mRNA-L, and a transcription level of an mRNA coding for a short isoform, mRNA-S, of an RBM39 protein.

16. The method as claimed in claim 1 comprising using a kit comprising at least one antibody suitable for determining (i) a level of production of a long isoform, ProtL, and (ii) a level of production of a short isoform, ProtS, of an RBM39 protein.

* * * * *